US00PP36915P2

(12) United States Plant Patent
Ralph Ballington, Jr.

(10) Patent No.: US PP36,915 P2
(45) Date of Patent: Sep. 2, 2025

(54) ***RHODODENDRON* PLANT NAMED 'NCB195'**

(50) Latin Name: ***Rhododendron* hybrid**
Varietal Denomination: NCB195

(71) Applicant: North Carolina State University, Raleigh, NC (US)

(72) Inventor: James Ralph Ballington, Jr., Cary, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 18/965,006

(22) Filed: Dec. 2, 2024

(51) Int. Cl.
*A01H 5/00* (2018.01)
*A01H 6/36* (2018.01)

(52) U.S. Cl.
USPC ..... Plt./239

(58) Field of Classification Search
USPC ..... Plt./238, 239
See application file for complete search history.

*Primary Examiner* — Susan McCormick Ewoldt

(57) ABSTRACT

A new and distinct cultivar of *Rhododendron* plant named 'NCB195' is disclosed, characterized by large, attractive, salmon/coral flowers with a yellow-orange blotch. Plants are compact, well-branched, and exhibit good disease resistance. The new cultivar is a *Rhododendron*, suitable for ornamental garden purposes.

2 Drawing Sheets

Latin name of the genus and species: *Rhododendron* hybrid.

Variety denomination: 'NCB195'.

BACKGROUND OF THE INVENTION

The new cultivar is a product of a planned breeding program by the inventor to develop new *Rhododendron* varieties with good disease resistance, compact habits, and attractive, long-lasting flowers. The seed parent is an unpatented internal selection of *Rhododendron atlanticum* x *calendulaceum* named 'B-108'. The pollen parent is the unpatented cultivar *Rhododendron* 'Red Velvet'. The crossing resulting in the cultivar was made in the year 1990 at a nursery in Cary, North Carolina.

*Rhododendron* 'NCB195' was found and selected during 1995 in Cary, North Carolina. The first asexual propagation of occurred in 2018 by softwood cuttings at the same nursery, and 'NCB195' has been found to retain its distinctive characteristics through successive asexual propagations over multiple generations.

SUMMARY OF THE INVENTION

The cultivar 'NCB195' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NCB195'. These characteristics in combination distinguish 'NCB195' as a new and distinct *Rhododendron* cultivar:

1. Large, attractive salmon/coral flowers with a yellow-orange blotch.
2. Compact, well-branched habit.
3. Very good leaf disease resistance.

4. Good resistance to *Phytophthora* root rot.
5. Good heat tolerance in warm, humid regions.

COMPARISON TO PARENT VARIETIES

'NCB195' is similar in most horticultural characteristics to the seed parent. Plants of the new cultivar 'NCB195' however differ in the following:

1. Flower color of the new cultivar is salmon/coral with a yellow-orange blotch, while the flower color of the seed parent is very pale yellow with pink overtones.
2. Plant habit of the new cultivar is compact, while the plant habit of the seed parent is somewhat spreading and irregular.
3. The new cultivar blooms approximately 2 weeks earlier than the seed parent.

'NCB195' is similar in most horticultural characteristics to the pollen parent. Plants of the new cultivar 'NCB195' however differ in the following:

1. Flower color of the new cultivar is salmon/coral with a yellow-orange blotch, while the flower color of the pollen parent is dark red.

COMMERCIAL COMPARISON

'NCB195' can be compared to the commercial cultivar *Rhododendron* 'Rosy Lights', unpatented. Plants of the new cultivar 'NCB195' are similar to plants of 'Rosy Lights' in most horticultural characteristics. Plants of the new cultivar 'NCB195', however, differ in the following:

1. Flower color of the new cultivar is salmon/coral with a yellow-orange blotch, while the flower color of this comparator is strictly bright pink.
2. Plants of the new cultivar are smaller at maturity than plants of this comparator.

BRIEF DESCRIPTION OF THE PHOTOGRAPHS

'NCB195' is illustrated by the accompanying photographs, which show the plant's form, foliage, and inflorescences. The colors shown are as true as can be reasonably obtained by conventional photographic procedures. Colors in the photographs may differ slightly from the color values cited in the detailed botanical description, which accurately describe the new hybrid *Rhododendron.*

DETAILED BOTANICAL DESCRIPTION

Figure 1:
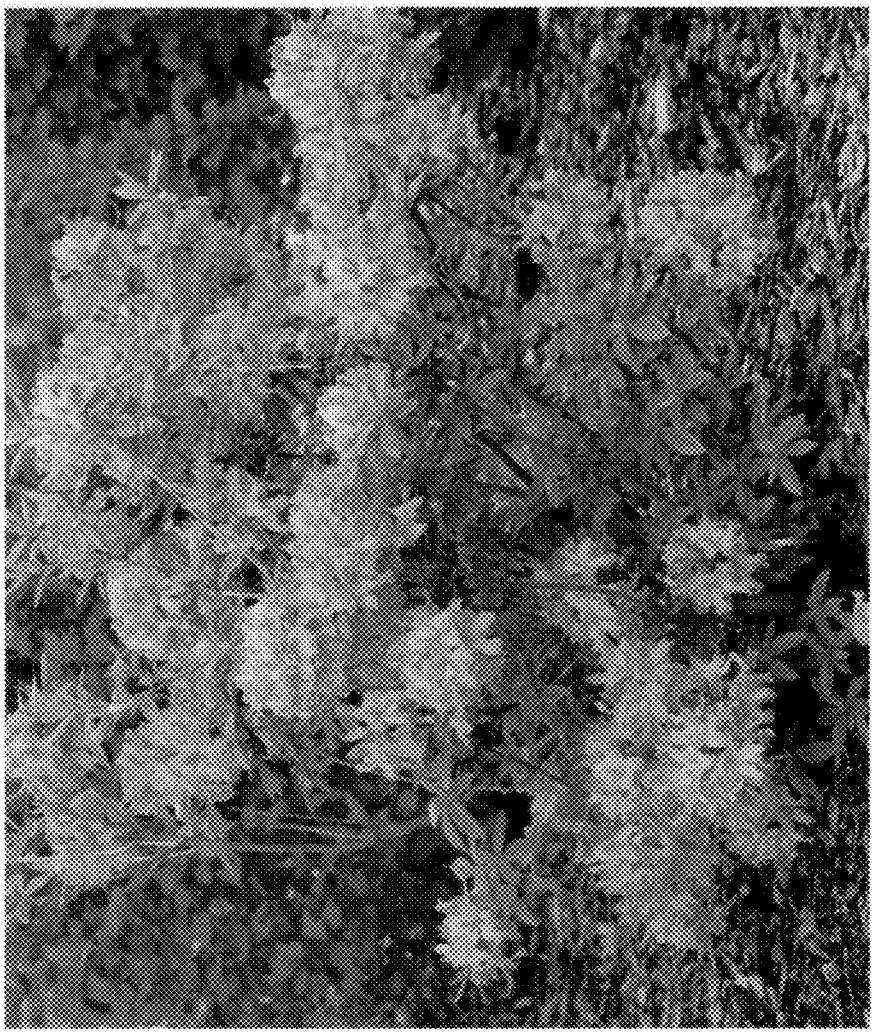
FIG. 1 is a photograph of a plant of 'NCB195' at approximately 2.5 years of age planted outdoors in Raleigh, NC.
Figure 2:
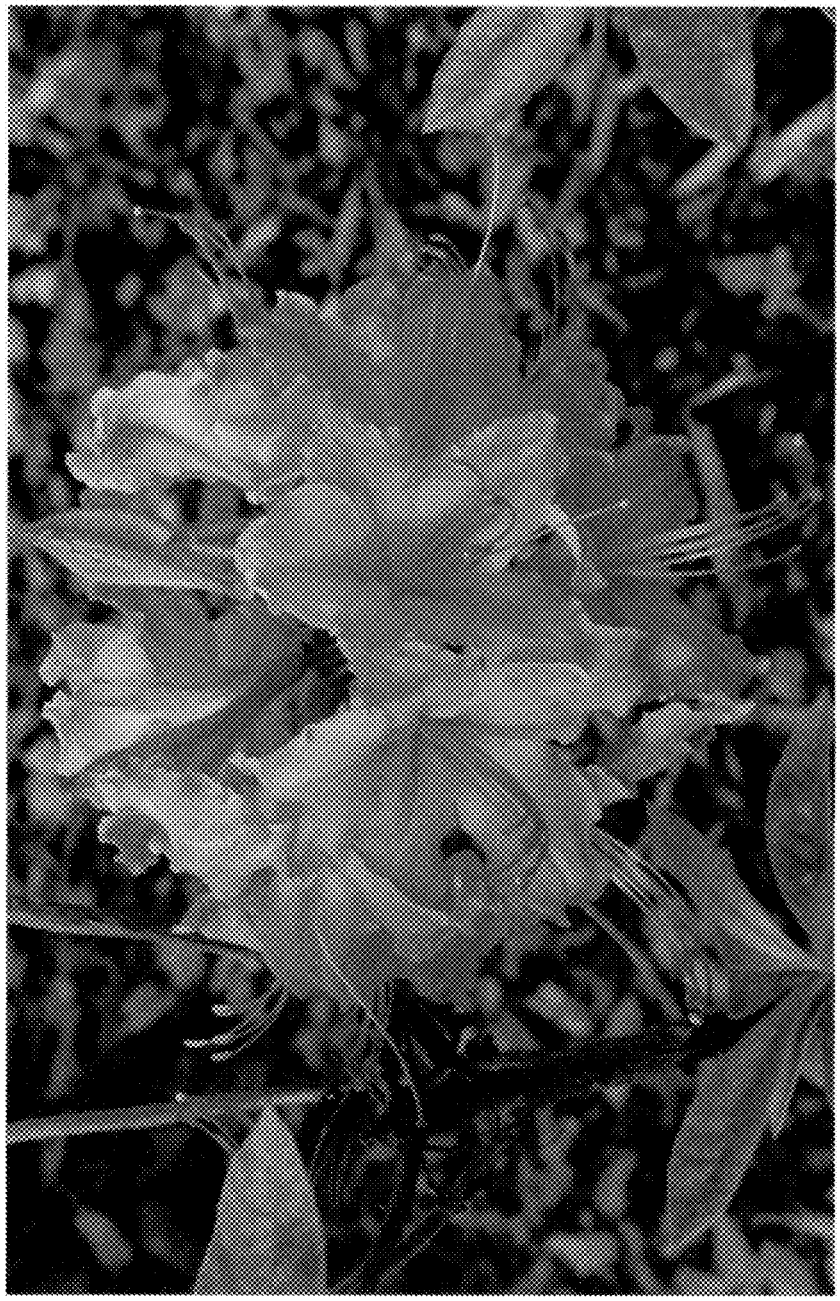
FIG. 2 is a photograph of a typical inflorescence of 'NCB195'.

The following is a detailed description of the botanical characteristics of the new and distinct *Rhododendron* 'NCB195'. The detailed description was taken on a 3-year-old container-grown plant in Grand Haven, Michigan in 2024. All colors cited herein refer to The Royal Horticultural Society Colour Chart (The Royal Horticultural Society (R.H.S.), London, 2015 Edition. Where specific dimensions, sizes, colors, and other characteristics are given, it is to be understood that such characteristics are approximations or averages set forth as accurately as is practicable.

Botanical classification: *Rhododendron* hybrid 'NCB195'.

PROPAGATION

Typical method: Softwood cuttings.

Root description: Sparse, fibrous, freely branching, thin. Off-white in color, not accurately measured with an R.H.S. chart.

Time to initiate rooting: 55 days in summer at 18° to 27° C.

Time to produce a rooted young plant: 90 days in summer at 18° to 27° C.

PLANT

Plant type: Perennial flowering shrub.

Plant shape: Upright, compact.

Growth habit: Upwards and slightly outwards.

Height: 80 cm.

Width: 75 cm.

Growth rate: Moderate to high.

Branching habit:

Stem:

- *Branching.*—Basal, some pinching required.
- *Number of lateral branches.*—About 20.
- *Shape.*—Rounded.
- *Color.*—Immature: Between RHS Yellow-Green 144C and 146C. Mature: RHS Brown 200D.
- *Length.*—40 to 60 cm.
- *Width.*—1 cm.
- *Aspect.*—30° to 60°.
- *Strength.*—Strong; old growth quite sturdy and rigid.
- *Pubescence.*—On new growth only.

Internode length: 1.5 cm.

Deciduous or evergreen: Evergreen.

FOLIAGE

Leaf:

- *Arrangement.*—Alternate, single.
- *Shape.*—Elliptic.
- *Length.*—7 cm.
- *Width.*—2.75 cm.
- *Apex.*—Acute.
- *Base.*—Attenuate.
- *Margin.*—Entire, ciliolate.
- *Color.*—Young, upper surface: RHS Yellow-Green 146A with slight tint of Greyed-Purple 185A at the margins. Young, under surface: RHS Yellow-Green 147B with slight tint of Greyed-Purple 185A at the margins. Mature, upper surface: RHS Yellow-Green 147A. Mature, under surface: RHS Yellow-Green 147C and 147D.
- *Texture.*—Upper surface: Lightly pubescent with small, coarse hairs. Lower surface: Glabrous, except for slight pubescence on midrib.
- *Venation.*—Pattern: Pinnate. Color, upper side: RHS Yellow-Green 146C. Color, under side: RHS Yellow-Green 146C.

Petiole:

- *Length.*—5 mm.
- *Diameter.*—1 mm.
- *Color.*—Upper side: RHS Yellow-Green 146C. Under side: RHS Yellow-Green 146C.
- *Texture.*—Lightly pubescent, both sides.

INFLORESCENCE

Natural flowering season: Spring (May).

Inflorescence type: Terminal raceme (truss).

Inflorescence height: 8 cm.

Inflorescence width: 12 cm.

Flowers per inflorescence: About 20 to 25.

Flowers per lateral stem: About 20.

Buds per lateral stem: About 5.

Flowers and buds per plant: About 500.

Fragrance: Sweet and musky, perfume-like; moderate to strong intensity.

Flowers:

- *Arrangement.*—Terminal raceme (truss).
- *Form.*—Funnel-shaped with whorled petals.
- *Habit.*—Racemes (trusses) at the terminal ends of lateral branches.
- *Aspect.*—Upright and outward.
- *Length.*—5 cm.
- *Diameter.*—5 cm.
- *Depth.*—6 cm.
- *Longevity.*—Individual flowers persist for 3-7 days, though the buds and flowers which comprise the truss have a staggered opening, leading to an inflorescence that persists for approximately two weeks.
- *Persistence.*—Self-cleaning.

Bud:

- *Length.*—4 cm.
- *Width.*—1.2 cm.
- *Shape.*—Spatulate with a prominent, acute, curved tip.
- *Color.*—RHS Greyed-Red 179B.

Petals:

- *Appearance.*—Soft and vibrant with slightly ruffled margins, with the bottom-most petal being slightly broader with a bright yellow-orange spot of color or "eye.".
- *Arrangement.*—Whorl (stellate).
- *Number.*—5.
- *Length.*—3 cm.
- *Width.*—Upper: 1.5 cm. Lower: 2 cm.
- *Shape.*—Upper: Elliptic. Lower: Broadly elliptic.
- *Apex.*—Upper: Acute. Lower: Obtuse.
- *Base.*—Fused.

*Margin*.—Slightly crenate or undulating, becoming more ruffled towards the tip.

*Color*.—When opening, upper side: RHS Orange-Red 31C with the bottom-most petal being predominately Orange 24B, darkening to Orange 24A towards throat. When opening, under side: RHS Red 37B, with the underside of the bottom-most petal being Yellow-Orange 16B. Fully opened, upper side: RHS Orange-Red 31C with the bottom-most petal being predominately Orange 24B, darkening to Orange 24A towards throat. Fully opened, under side: RHS Red 37B, with the underside of the bottom-most petal being Yellow-Orange 16B. Fading, upper side: RHS Red 55C with the bottom-most petal possessing a Yellow-Orange 19A spot or "eye". Fading, under side: RHS Red 55C to 55D.

*Texture*.—Upper: Glabrous, soft and silky. Lower: Glabrous, soft and silky.

Throat:

*Diameter*.—1 cm.

*Texture*.—Glabrous.

Tube:

*Length*.—2 cm.

*Diameter*.—5 mm.

*Texture*.—Slightly pubescent with small, coarse hairs.

Sepals:

*Number*.—5.

*Arrangement*.—Whorl (stellate).

*Length*.—3 mm.

*Width*.—2 mm.

*Shape*.—Elliptic.

*Apex*.—Obtuse.

*Base*.—Fused.

*Margin*.—Entire.

*Color*.—Mature, upper side: RHS Yellow-Green 144A. Mature, under side: RHS Yellow-Green 144A.

*Texture*.—Upper side: Glabrous. Under side: Lightly pubescent.

Calyx:

*Length*.—3 mm.

*Diameter*.—3 mm.

*Shape*.—Collar-like.

Peduncle.

*Length*.—1.2 cm.

*Diameter*.—2 mm.

*Angle*.—60° to 90° relative to lateral stem.

*Strength*.—Good.

*Color*.—RHS Yellow Green 144A.

*Texture*.—Lightly pubescent.

Pedicel:

*Length*.—1.5 cm.

*Diameter*.—2 mm.

*Angle*.—45° relative to peduncle.

*Strength*.—Good.

*Texture*.—Lightly pubescent.

*Color*.—RHS Yellow Green 144A.

REPRODUCTIVE ORGANS

Gynoecium:

*Pistil number*.—1.

*Pistil length*.—6 cm.

*Stigma shape*.—Elliptic.

*Stigma color*.—RHS Green 137A.

*Style length*.—6 cm.

*Style color*.—RHS Red 37A.

*Ovary color*.—RHS Yellow-Green 144A.

Androecium:

*Stamen number*.—5.

*Anther shape*.—Elliptic.

*Anther length*.—2 mm.

*Anther color*.—RHS Yellow-Orange 14D.

*Filament length*.—5 cm.

*Filament color*.—RHS Red 55C.

*Amount of pollen*.—Moderate.

*Pollen color*.—RHS Yellow-Orange 14D.

OTHER CHARACTERISTICS

Fruit and seed: Not observed.

Disease and pest resistance: Foliage is very healthy and is generally unplagued by pathogens common to *Rhododendron*, including powdery mildew, leaf spots and rust. 'NCB195' displays good resistance to *Phytophthora* root rot.

Temperature tolerance: Tolerant to USDA Zones 4-8. Excellent tolerance to rain.

What is claimed is:

1. A new and distinct cultivar of *Rhododendron* plant named 'NCB195' as herein illustrated and described.

* * * * *